US006808907B2

(12) United States Patent
Honma et al.

(10) Patent No.: US 6,808,907 B2
(45) Date of Patent: Oct. 26, 2004

(54) METHOD AND APPARATUS FOR PRODUCING POLYHYDROXYALKANOATE

(75) Inventors: Tsutomu Honma, Kanagawa (JP); Etsuko Sugawa, Kanagawa (JP); Tetsuya Yano, Kanagawa (JP); Tsuyoshi Nomoto, Tokyo (JP); Takeshi Imamura, Kanagawa (JP); Tomohiro Suzuki, Kanagawa (JP); Takashi Kenmoku, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 191 days.

(21) Appl. No.: 10/105,332

(22) Filed: Mar. 26, 2002

(65) Prior Publication Data

US 2003/0032151 A1 Feb. 13, 2003

(30) Foreign Application Priority Data

| Mar. 27, 2001 | (JP) | ................................... | 2001/089980 |
| Apr. 10, 2001 | (JP) | ................................... | 2001/111273 |
| Apr. 10, 2001 | (JP) | ................................... | 2001/111274 |
| May 30, 2001 | (JP) | ................................... | 2001/162448 |

(51) Int. Cl.$^7$ ............................. C12P 7/62; C08G 63/78
(52) U.S. Cl. ..................... 435/135; 528/272; 528/274; 528/354; 528/358; 528/361
(58) Field of Search ............................. 435/135, 138; 528/272, 274, 354, 358, 361

(56) References Cited

U.S. PATENT DOCUMENTS

| 4,138,291 | A | | 2/1979 | Lafferty ........................ 195/47 |
| 4,310,655 | A | * | 1/1982 | Reimschuessel et al. ... 528/176 |
| 4,393,167 | A | | 7/1983 | Holmes et al. ................ 525/64 |
| 5,110,980 | A | | 5/1992 | Ramsay et al. ............. 560/185 |
| 5,135,859 | A | | 8/1992 | Witholt et al. ............... 435/135 |
| 5,292,860 | A | | 3/1994 | Shiotani et al. ............. 528/361 |
| 5,334,698 | A | | 8/1994 | Witholt et al. ............... 528/354 |
| 5,451,456 | A | * | 9/1995 | Marchessault et al. ...... 428/327 |
| 5,691,174 | A | | 11/1997 | Liddell et al. ............... 435/135 |

FOREIGN PATENT DOCUMENTS

| EP | 0 046 335 A2 | 2/1982 |
| EP | 0 052 459 A1 | 5/1982 |
| EP | 0870837 | 10/1998 |
| JP | 57-174094 A | 10/1982 |
| JP | 63-226291 A | 9/1988 |
| JP | 5-74492 A | 3/1993 |
| JP | 5-93049 A | 4/1993 |
| JP | 6-15604 B2 | 3/1994 |
| JP | 7-14352 B2 | 2/1995 |
| JP | 7-177894 A | 7/1995 |
| JP | 7-265065 A | 10/1995 |
| JP | 08-19227 B2 | 2/1996 |
| JP | 8-508881 A | 9/1996 |
| JP | 2642937 B2 | 5/1997 |
| JP | 9-191893 A | 7/1997 |
| JP | 2000-72865 A | 3/2000 |
| JP | 2000-166587 A | 6/2000 |
| WO | WO 94/24302 | 10/1994 |
| WO | WO 98/07879 | 2/1998 |

OTHER PUBLICATIONS

Hahn et al "Biotechnol. Tech." (1993) 7,3, 209–12.*
Gross, et al.; "Cyanophenoxy–Containing Microbial Polyesters . . . Biodegradability"; Polymer International, vol. 39 (1996) pp. 205–213.
Kim, et al.; "Bioengineering of poly(β–hydroxyalkanoates) . . . substituents"; Can. J. Microbiol. 41, (Suppl. 1): 32–43 (1995).
Biodegradable Plastics Handbook, edited by A Study Group of Biodegradable Plastics, NTS, Inc., pp. 178–197 (1995).
Middelberg, et al.; "Size Analysis . . . *Escherichia Coli* "; Biotechnology Letters, 17, 2 (1995), 205–210.
Ling, et al.; "Pilot–scale extraction . . . and centrifugation"; Bioseparation, 7, 1 (1997), 9–15.
"Omnilabo Laboratorium Production"; publ. by Omnilabo Int'l BV, (2000), XP–002246213.
Middelberg, et al.; "Process–scale . . . Microorganisms"; Biotechnology Advances, 13, 3 (1995), 491–551.
Choi, J., et al.; "Factors affecting . . . bacterial fermentation"; App. Microbiol Biotechnol, 51, (1999), 13–21.
Hahn, et al.; "Optimization of . . . and Chloroform"; Biotechnology and Bioengineering, 44, 2 (1994), 256–261.
Choi, J., et al.; "Process analysis . . . by fermentation"; Biopress Engineering 17, 6 (1997), 335–342.
Steinbüchel, et al.; "Diversity of . . . acids"; FEMS Microbiology Letters, 128, (1995), 219–228.
Braunegg, et al.; "Polyhyroxyalkoanates . . . aspects"; Journal of Biotechnology, 65, 2–3 (1998), 127–161.
K. Fritzsche et al., "An Unusual Bacterial Polyester with a Phenyl Pendant Group," 191 *Makromol. Chem.* 1957–1965 (1990).

(List continued on next page.)

*Primary Examiner*—Herbert J. Lilling
(74) *Attorney, Agent, or Firm*—Fitzpatrick, Cella, Harper & Scinto (57) ABSTRACT

The present invention provides a method for producing highly purified polyhydroxyalkanoate (PHA) with high yield, by removing cell components other than PHA from cells containing PHA. Moreover, the present invention provides a method for simply removing or reducing chlorine remained in the collected PHA particles, when a treatment with an oxidizing agent containing hypochlorite is performed in the production of PHA as described above. One of the above-described methods comprises a step of treating cells containing polyhydroxyalkanoate with an oxidizing agent containing at least hypochlorite, a step of separating the treated cells into a water-soluble fraction and a water-insoluble fraction, and a step of reducing chlorine remained in the water-insoluble fraction. The step of reducing chlorine may be a step of washing the water-insoluble fraction with a hot water, thiosulfate solution or polar solvent solution containing at least an organic polar solvent in which polyhydroxyalkanoate is insoluble.

15 Claims, 1 Drawing Sheet

OTHER PUBLICATIONS

Won Ho Park et al., "Epoxidation of Bacterial Polyesters with Unsaturated Side Chains. I. Production and Epoxidation of Polyesters From 10–Undecanoic Acid," 31 *Macromol.* 1480–1486 (1998).

Won Ho Park et al., "Epoxidation of Bacterial Polyesters with Unsaturated Side Chains. II. Rate of Epoxidation and Polymer Properties," 36 *J. Polym. Sci.* 2381–2387 (1998).

Helmut Ritter et al., "Bacterial Production of Polyesters Bearing Phenoxy Groups in the Side Chain, 1 Poly(3–hydroxy–5–phenoxypentanoate–co–3–hydroxy–9–phenoxy–nonanoate) from *Pseudomonas oleovorans*," 195 *Macromol. Chem. Phys.* 1665–1672 (1994).

B.A. Ramsay et al., "Effect of Nitrogen Limitation on Long–Side–Chain Poly–β–Hydroxyalkanoate Synthesis by *Pseudomonas resinovarans*," 58(2) *Appl. Environ. Microbiol.* 744–746 (1992).

Y.B. Kim et al., "Preparation and Characterization of Poly(β–hydroxyalkanoates) Obtained from *Pseudomonas oleovorans* Grown with Mixtures of 5–Phenylvaleric Acid and n–Alkanoic Acids," 24 *Macromol.* 5256–5260 (1991).

Yasuo Takagi et al., "Biosynthesis of Polyhdroxyalkanoate with a Thiophenoxy Side Groups Obtained from *Pseudomonas putida*," 32 *Macromol.* 8315–8318 (1999).

D.H. Williamson et al., "The Isolation and Estimation of the Poly–β–hydroxy–butyrate Inclusions of *Bacillus* Species," 19 *J. gen. Microbiol.* 198–209 (1958).

Joanne M. Curley et al., "Production of Poly(3–hydroxyalkanoates) Containing Aromatic Substituents by *Pseudomonas oleovorans*," 29 *Macromol.* 1762–1766 (1996).

Suzette M. Aróstegui et al., "Bacterial Polyesters Produced by *Pseudomonas oleovorans* Containing Nitrophenyl Groups," 32 *Macromol.* 2889–2895 (1999).

* cited by examiner

FIGURE

METHOD AND APPARATUS FOR PRODUCING POLYHYDROXYALKANOATE

BACKGROUND OF THE INVENTION

1. Field of the Invention

The present invention relates to a method for producing polyhydroxyalkanoate (which is also referred to as "poly-3-hydroxyalkanoic acid", and hereinafter abbreviated as "PHA" at times), using a microorganism having an ability to produce and accumulate PHA in a cell thereof, or a higher organism such as a plant cell, in which PHA production has enabled by introduction of a PHA synthesis gene.

More specifically, the present invention relates to a method for producing PHA, which comprises a step of removing cell components other than PHA by treating cells containing PHA with an oxidizing agent, which can efficiently remove cell components other than PHA with a few steps, at a low cost, and obtain highly purified PHA with high yield. Further, the present invention relates to a method for producing PHA, wherein PHA containing a reduced amount of residual chlorine or no residual chlorine can be obtained.

Furthermore, the present invention relates to an apparatus, with which the above-described methods for producing PHA can be carried out.

2. Related Background Art

Up till now, it has been reported that a large number of microorganisms produce and accumulate poly-3-hydroxybutyric acid (hereinafter abbreviated as "PHB" at times) or other PHAs in cells thereof (Biodegradable Plastic Handbook, ed. by A Study Group of Biodegradable Plastics, NTS, Inc., p. 178–197). As the conventional plastics, these polymers can also be used for production of various products by melt processing, etc. Moreover, these polymers have an advantage of biodegradability to be completely decomposed by microorganisms in the nature. Therefore, unlike many synthetic high polymers previously used, these polymers do not remain in the natural environment and cause no pollution, and they require no incineration treatment, so they can be useful materials in terms of prevention of air pollution or global warming. Further, these polymers are excellent in biocompatibility, and so it is expected that they will be applied as medical soft materials, etc. It is known that the PHA produced by microorganisms can have various compositions or structures depending on the type of microorganisms used for the production, the composition of medium, culture conditions, etc., and researches on the control of the composition or structure have been made mainly from the viewpoint of improvement of the physical properties of PHA.

For example, it has been reported that *Alcaligenes eutrophus* H16 (ATCC No. 17699) and mutants thereof produce a copolymer of 3-hydroxybutyric acid and 3-hydroxyvaleric acid in various composition ratios by varying carbon sources when they are cultured (Japanese Patent Publication Nos. 6-15604, 7-14352, 8-19227, etc.). Japanese Patent Application Laid-Open No. 5-74492 discloses a method for allowing microorganisms of *Methylobacterium* sp., *Paracoccus* sp., *Alcaligenes* sp., *Pseudomonas* sp. to produce a copolymer of 3-hydroxybutyric acid and 3-hydroxyvaleric acid by contacting them with primary alcohol containing 3 to 7 carbon atoms. Japanese Patent Application Laid-Open No. 9-191893 discloses that *Comamonas acidovorans* IF013852 produces a polyester having 3-hydroxybutyric acid unit and 4-hydroxybutyric acid unit by performing culture using gluconic acid and 1,4-butanediol as carbon sources.

Japanese Patent No. 2642937 discloses that *Pseudomonas oleovorans* ATCC 29347 produces PHA having a 3-hydroxyalkanoic acid unit containing 6 to 12 carbon atoms, where noncyclic aliphatic hydrocarbon is provided thereto as a carbon source. Japanese Patent Application Laid-Open Nos. 5-93049 and 7-265065 disclose that *Aeromonas caviae* produces a copolymer of two components, 3-hydroxybutyric acid and 3-hydroxyhexanoic acid, by performing culture using oleic acid or olive oil as a carbon source.

The above described PHAs are all PHAs consisting of monomer units having an alkyl group on a side chain, which are synthesized by β-oxidation of carbohydrate etc. or fatty acid synthesis from a sugar by a microorganism and each of these PHAs is what is called "usual PHA".

It has been reported that some types of microorganisms produce, PHA having various substituents other than alkyl groups introduced into side chains thereof, that is what is called "unusual PHA", and using such means, an attempt to improve the physical properties of the PHA produced by microorganisms has been started. Moreover, where a broader application of the PHA produced by microorganism, e.g. application as a functional polymer is considered, the "unusual PHA" is extremely useful. Examples of substituents include a substituent comprising an aromatic ring (a phenyl group, a phenoxy group, a benzoyl group, etc.), an unsaturated hydrocarbon, an ester group, an allyl group, a cyano group, a halogenated hydrocarbon, an epoxide, etc. Of these, particularly, intensive studies on PHA having an aromatic ring have been progressing.

(a) Substituents comprising a phenyl group or a partially substituted phenyl group Makromol. Chem., 191, 1957–1965 (1990) and Macromolecules, 24, 5256–5260 (1991) report that *Pseudomonas oleovorans* produces PHA comprising 3-hydroxy-5-phenylvaleric acid as a unit from 5-phenylvaleric acid as a substrate. Macromolecules, 29, 1762-1766 (1996) reports that *Pseudomonas oleovorans* produces PHA comprising 3-hydroxy-5-(4'-tolyl)valeric acid as a unit from 5-(4'-tolyl)valeric acid as a substrate. Macromolecules, 32, 2889–2895 (1999) reports that *Pseudomonas oleovorans* produces PHA comprising 3-hydroxy-5-(2',4'-dinitrophenyl)valeric acid and 3-hydroxy-5-(4'-nitrophenyl)valeric acid as units from 5-(2', 4'-dinitrophenyl)valeric acid as a substrate.

(b) Substituents comprising a phenoxy group or a partially substituted phenoxy group Macromol. Chem. Phys., 195, 1665–1672 (1994) reports that *Pseudomonas oleovorans* produces a PHA copolymer of a 3-hydroxy-5-phenoxyvaleric acid unit and a 3-hydroxy-9-phenoxynonanoic acid unit, from 11-phenoxyundecanoic acid as a substrate. Japanese Patent No. 2989175 discloses inventions regarding: a homopolymer consisting of a 3-hydroxy-5-(monofluorophenoxy)pentanoate (3H5(MFP)P) unit or a 3-hydroxy-5-(difluorophenoxy)pentanoate (3H5(DFP)P) unit; a copolymer comprising at least a 3H5(MFP)P unit or a 3H5(DFP)P unit; and a method for producing the above-described polymers, using *Pseudomonas putida* of *Pseudomonas* sp. that synthesizes these polymers. The publication states that the effect of the inventions is to provide stereoregularity and water repellency while retaining a high melting point and good workability. Moreover, Japanese Patent Application Laid-Open No. 2000-72865 reports that *Pseudomonas putida* 27N01 produces PHA comprising various types of 3-hydroxyfluorophenoxyvaleric acid units.

In addition to such fluorine-substituted forms, studies on cyano- or nitro-substituted forms have also been progressed.

Can. J. Microbiol., 41, 32–43 (1995) and Polymer International, 39, 205–213 (1996) report the production of PHA comprising 3-hydroxy-p-cyanophenoxyhexanoic acid or 3-hydroxy-p-nitrophenoxyhexanoic acid as a monomer unit from octanoic acid and p-cyanophenoxyhexanoic acid or p-nitrophenoxyhexanoic acid as substrates, using *Pseudomonas oleovorans* ATCC 29347 and *Pseudomonas putida* KT 2442.

These reports are useful to obtain polymers having physical properties derived from PHA having an aromatic ring on a side chain thereof, unlike a usual PHA having an alkyl group on a side chain.

As a new category, not only regarding change of physical properties, but also a study for producing PHA having a suitable functional group on a side chain thereof to create a new function using the functional group, is progressing.

For example, Macromolecules, 31, 1480–1486 (1996), Journal of Polymer Science: Part A: Polymer Chemistry, 36, 2381–2387 (1998), etc. report that PHA comprising a highly reactive epoxy group at the terminus of a side chain thereof was synthesized by synthesizing PHA comprising a unit having a vinyl group at the terminus of the side chain and then performing epoxidation with an oxidizing agent. Further, other than a vinyl group, as an example of synthesizing PHA comprising a unit having thioether that is expected to have a high reactivity, Macromolecules, 32, 8315–8318 (1999) reports that *Pseudomonas putida* 27N01 produces a PHA copolymer comprising a 3-hydroxy-5-thiophenoxyvaleric acid unit and a 3-hydroxy-7-thiophenoxyheptanoic acid unit from 11-thiophenoxyvaleric acid as a substrate.

It is known that microorganisms accumulate the produced PHA in their cells in the form of particles. To separate the PHA accumulated in the cells from microorganism cells and purify it, there are both a method involving extraction of PHA with a chlorine containing organic solvent such as chloroform or dichloromethane and a method for obtaining PHA particles by solubilizing cell components other than PHA for removal. The former solvent extraction method is an excellent method for simply extracting and separating PHA with high purity, but at an industrial production level, production scale increases, causing a problem regarding a need for a large amount of organic solvent (it is pointed out that a chlorine containing organic solvent used such as chloroform causes an environmental or health problem when the solvent volatilizes or transpires). Moreover, when PHA should be obtained in the form of particles, the method involving solvent extraction can not be employed.

On the other hand, as the latter method involving solubilization of cell components other than PHA for removal, there is known a method comprising solubilizing cell components other than PHA by a treatment with an agent such as hypochlorite or hydrogen peroxide, and collecting insoluble PHA particles by solid-liquid separation. For example, J. Gen. Microbiology, 19, 198–209 (1958) reports a method for separating and purifying polymers by treating microorganism cells with an alkali solution of sodium hypochlorite. Japanese Patent Application Domestic Publication No. 8-508881 discloses a method for separating PHA from a cell by treating a PHA accumulating cell with endopeptidase, then treating with a suitable chelating agent, and further treating with hydrogen peroxide.

As another method, Japanese Patent Application Laid-Open No. 57-174094 discloses a method for separating PHA from a microorganism cell by heating and pressurizing a PHA accumulating cell, and then releasing the pressure to crush the cell. Japanese Patent Application Laid-Open No. 63-226291 discloses a method for separating PHA, which comprises converting cell bodies to spheroplasts, crushing them by sonication, performing centrifugal separation, and separating PHA in the uppermost layer formed after the centrifugal separation.

These methods are extremely useful even when PHA is required to be obtained in the form of particles.

However, in the above-stated treatments, there are problems that operation is complicated and that enzyme, acid or alkali is used and is likely to remain after the use therefore a method for more simply collecting PHA with high purity is desired.

When compared with methods using other treating agents, a method using an oxidizing agent such as hypochlorite or hydrogen peroxide, needs moderate treatment conditions with simple steps, and impurities from cells are seldom mixed, so highly purified PHA can be obtained in the form of particles. Thus, this is an excellent method having many practical advantages such as low cost, but it has problems to be solved as stated below.

For example, it has been considered that a method for collecting PHA accumulated in cells in the form of particles by treating the cells with hypochlorite such as sodium hypochlorite, is not adequate to practical use, since it has problems that molecular weight is reduced depending on the structure of PHA, and that a considerable amount of chlorine is remained in the collected PHA (for example, see Japanese Patent Application Laid-Open No. 7-177894).

According to studies of the present inventors, it was found that this residual chlorine is released quickly, when PHA is heated. So, when a desired processed product is made from PHA particles obtained by using such a hypochlorite treatment, if a large amount of chlorine is released in a heating process thereof, it is strongly concerned that the released chlorine becomes a factor of pollution of work environment, etc. In addition, according to studies of the present inventors, it has also been clarified that the residual chlorine contained in the PHA particles cannot be removed sufficiently by a usual treatment such as washing with water. A conclusion is reached from the studies that, although the residual chlorine is strongly retained by PHA particles, it is released at a time by performing a heating process, and thereby the above-stated large amount of chlorine is observed.

Accordingly, in a method for producing PHA involving a treatment with hypochlorite in the production process, the development of means for reducing residual chlorine strongly retained by PHA particles is an extremely important challenge in developing and using PHA on a commercial scale, especially in obtaining and using the PHA in the form of particles.

On the other hand, in a method for collecting PHA accumulated in cells by treating the cells with a peroxide compound such as hydrogen peroxide or sodium peroxide, increase of purity of the collected PHA is an extremely important challenge in developing and using PHA on a commercial scale.

Therefore, an object of the present invention is, when PHA is produced by treating with an oxidizing agent, to solve the above-stated problems in the prior art and to provide a method for producing PHA which comprises efficiently removing cell components other than PHA with a few steps, at a low cost, so as to obtain highly purified PHA with high yield.

Moreover, another object of the present invention is, when PHA is produced by treating with an oxidizing agent containing hypochlorite, to provide a method for producing PHA which comprises a step of removing or reducing chlorine remained in the collected PHA particles by simple means with a good reproducibility.

SUMMARY OF THE INVENTION

As a result of thorough studies on a method for producing highly purified PHA with high yield by efficiently removing cell components other than PHA from cells containing PHA, with a few steps, at a low cost, the present inventors have accomplished the following invention.

That is to say, the present invention relates to a method for producing PHA by treating cells containing PHA with an oxidizing agent to remove cell components other than PHA, which comprises a step of treating the cells with an oxidizing agent comprising at least hypochlorite, a step of separating the treated cells into a water-soluble fraction and a water-insoluble fraction, and a step of reducing chlorine remained in the water-insoluble fraction.

Specifically, the present invention relates to a method for producing PHA by treating cells containing PHA with an oxidizing agent to remove cell components other than PHA, which comprises a step of treating the cells with an oxidizing agent comprising at least hypochlorite, a step of separating the treated cells into a water-soluble fraction and a water-insoluble fraction, and a step of washing the water-insoluble fraction with a hot water.

Moreover, the present invention relates to a method for producing PHA by treating cells containing PHA with an oxidizing agent to remove cell components other than PHA, which comprises a step of treating the cells with an oxidizing agent comprising at least hypochlorite and a step of washing the obtained PHA with an aqueous thiosulfate solution.

Furthermore, the present invention relates to a method for producing PHA by treating cells containing PHA with an oxidizing agent to remove cell components other than PHA, which comprises a step of treating the cells with an oxidizing agent comprising at least hypochlorite and a step of washing the obtained PHA with a polar solvent solution comprising at least an organic polar solvent in which the PHA is insoluble.

Still more, the present invention relates to a method for producing PHA, comprising a step of obtaining a crushed product by crushing cells containing PHA, a step of separating the crushed product into a water-soluble fraction and a water-insoluble fraction and a step of treating the water-insoluble fraction with an oxidizing agent.

Still further, the present invention relates to an apparatus with which the above-described method for producing PHA can be carried out.

DESCRIPTION OF THE PREFERRED EMBODIMENTS

Figure 1:
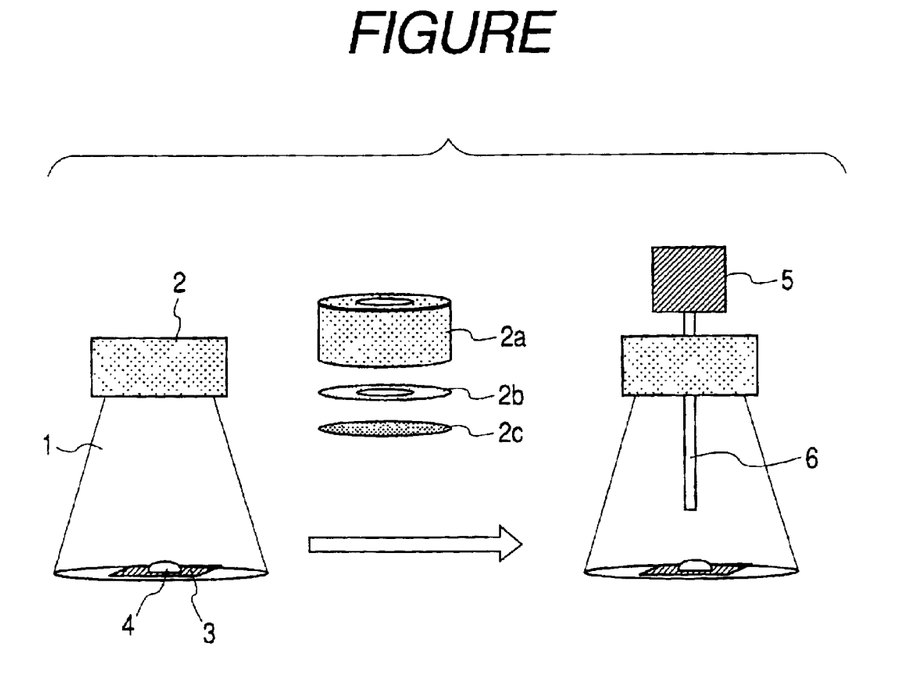
FIGURE is a view showing a method for determining chlorine concentration described in Examples 1 and 2.

According to the method for producing PHA of the present invention, PHA of interest can be biosynthesized and accumulated in cells, using a microorganism having an ability to produce the PHA, or a higher organism such as a plant cell, in which PHA production has enabled by introduction of a PHA synthesis gene of the microorganism by gene recombination technique. Accordingly, the term "cell" (also referred to as "biocell" or "organism cell") means not only microorganism cells, but also cells of a higher organism such as a plant cell, in which PHA production has enabled by intorduction of a PHA synthesis gene.

As the above-stated microorganism having an ability to produce PHA, any microorganism can be used as long as it has a desired PHA production ability, and examples of such a microorganism include Ralstonia eutropha TB64 that will be used in Examples of the present specification, *Pseudomonas oleovorans* ATCC 29347 (furnished from American Type Culture Collection), *Pseudomonas cichorii* YN2, *Alcaligenes* sp. TL2, etc.

The TB64 strain is disclosed in Japanese Patent Application Laid-Open No. 2000-166587, and this strain is deposited under the Budapest Treaty on the International Recognition of the Deposit of Microorganisms for the Purposes of Patent Procedure with International Patent Organism Depositary in National Institute of Advanced Industrial Science and Technology, an Independent Administrative Institution (the former Patent Microorganism Depositary Center of National Institute of Bioscience and Human-Technology, Agency of Industrial Science and Technology, the Ministry of International Trade and Industry) under accession No. FERM BP-6933.

The YN2 strain is deposited under the Budapest Treaty on the International Recognition of the Deposit of Microorganisms for the Purposes of Patent Procedure with the International Patent Organism Depositary in National Institute of Advanced Industrial Science and Technology, under accession No. FERM BP-7375. The bacteriological properties of YN2 can be listed as follows.

Bacteriological Properties of Strain YN2
(1) Morphological Properties
Shape and size of cells: rod, 0.8 $\mu$m×1.5 to 2.0 $\mu$m
Polymorphism of cells: negative
Mobility: motile
Sporulation: negative
Gram staining: negative
Colony shape: circular; entire, smooth margin; low convex; smooth surface; glossy; translucent
(2) Physiological Properties
Catalase: positive
Oxidase: positive
O/F test: oxidative (non-fermentative)
Nitrate reduction: negative
Indole production: positive
Acid production from glucose: negative
Arginine dihydrolase: negative
Urease: negative
Esculin hydrolysis: negative
Gelatin hydrolysis: negative
$\beta$-Galactosidase: negative
Fluorescent pigment production of King's B agar: positive
Growth under 4% NaCl: positive (weak growth)
Poly-p-hydroxybutyrate accumulation: negative (*)
Tween 80 hydrolysis: positive
(*) Colonies cultured on nutrient agar were stained with Sudan Black for determination.
(3) Substrate Assimilation
Glucose: positive
L-Arabinose: positive
D-Mannose: negative
D-Mannitol: negative
N-Acetyl-D-glucosamine: negative
Maltose: negative
Potassium gluconate: positive
n-Caprate: positive
Adipate: negative dl-Malate: positive
Sodium citrate: positive
Phenyl acetate: positive The TL2 strain is deposited under the Budapest Treaty on the International Recognition of the Deposit of Microorganisms for the Purposes of Patent Procedure with the Patent Organism Depositary of the National Institute of Advanced Industrial Science and Technology, under accession No. FERM BP-6913.

In the method of the present invention, insoluble PHA produced in these cells is accumulated in the form of particles. When these PHA particles are collected by solid-liquid separation, admixed impurities consisting of cell components other than PHA is solubilized by treating with an oxidizing agent, so that only water-insoluble PHA particles are separated as a solid phase component.

That is to say, in the method of the present invention, there is used means, wherein cells accumulating PHA are collected from a culture solution after culture, and these cells are suspended in a treatment solution containing an oxidizing agent, followed by a reaction for a certain period under certain conditions in the treatment solution, so as to solubilize and remove cell components other than PHA, thereby separating PHA particles from the cells. Examples of an oxidizing agent to be used in this means include hypochlorite and a peroxide compound.

Examples of hypochlorite used in the method of the present invention include potassium hypochlorite (KClO), calcium hypochlorite ($Ca(OCl)_2$), sodium hypochlorite (NaClO), and these can be selected and used as appropriate.

The concentration of hypochlorite dissolved in a treatment solution is preferably set within a range of 0.5% to 12.0%, desirably 1.5% to 5.0% as an effective chlorine concentration in the solution. For example, where a commercially available sodium hypochlorite solution is used as hypochlorite, the concentration of sodium hypochlorite is desirably set around 4% (about 1.7% as an effective chlorine concentration) to about 6% (about 2.5% as an effective chlorine concentration). Moreover, the amount of the treatment solution is preferably set within a range of 50 ml to 300 ml per g dry weight of cells to perform a treatment. The treatment temperature is desirably set within a range of 0° C. to 10° C. to perform a treatment, since if the temperature is higher than room temperature (around 20° C.), even PHA itself may be reacted and provide partial hydrolysis, resulting in reduction of the molecular weight of PHA. In some cases, the contact of sodium hypochlorite with cells may generate heat, so attention should be paid necessarily. When the concentration of hypochlorite and the temperature condition are selected as stated above, a treatment period is set within a range of 1 hour to 5 hours, usually about 2 hours to attain a sufficient solubilization treatment. Where the treatment period is set at less than 1 hour, solubilization of cell components other than PHA is insufficient, and where the treatment is carried out for more than 5 hours, it causes reduction of the molecular weight of PHA, so attention should be paid.

Examples of the peroxide compound used in the present invention include organic peroxides such as hydrogen peroxide, perbenzoic acid, metachloroperbenzoic acid, performic acid, peracetic acid, monoperoxyphthalic acid and trifluoroperacetic acid, and esters thereof. Of these, either hydrogen peroxide or sodium percarbonate is desirably used, since it can easily be used as a solution and provides a relatively moderate reaction. Hydrogen peroxide is extremely useful in terms of enhancement of the purity of the collected PHA, since it provides no residues after a treatment, but this compound may have a possibility that the structure is changed by oxidation depending on the unit structure of PHA. In such a case, sodium percarbonate is desirably used, that provides a more moderate reaction.

The concentration of hydrogen peroxide used in the above-described method is desirably within a range of 3.0% to 31.0%, and the concentration of sodium percarbonate is desirably within a range of 5.0% to 20.0%.

Where these peroxide compounds are used, the treatment temperature is desirably within a range of 80° C. to 100° C. If the temperature is set below the above range, it has little effect and the purity of the collected product becomes low. If the temperature is set beyond the above range, the structure of the compound may be altered. The reaction time is set at 30 minutes to 2 hours, more desirably about 1 hour.

After completion of the above-described reaction of solubilization treatment, PHA particles in the treatment solution can be collected by any solid-liquid separation means, as long as it enables to effectively separate the PHA particles from solubilized cell components that coexist therewith. For example, PHA particles can be separated from soluble fractions by centrifugal separation method. PHA in this time point is in the form of fine particles suspended in an aqueous solution. The operation of centrifugal separation should be carried out while maintaining the form of PHA fine particles, so that the subsequent dechloridation treatment is carried out with high efficiency. That is, centrifugal separation is desirably carried out with a temperature of about 0° C. to about 10° C., preferably about 0° C. to about 5° C.

Moreover, more desirably, there is added a step of further washing PHA particles collected by centrifugal separation method with a purified water such as a deionized water, distilled water or pure water, so as to sufficiently remove admixed components which are likely to be contained in small amounts. The above-described washing step is desirably carried out two or three times. Especially, when sodium percarbonate is used as a peroxide compound, attention is needed for avoiding the residue of sodium percarbonate.

Where extremely highly purified PHA is required to be obtained, after separating and washing PHA, for example, a chemical treatment using enzyme, an oxidizing agent, a surfactant, or a combined use thereof, can also be performed.

Where a step of crushing cells is further added before the above-described step of treating with an oxidizing agent, PHA can be separated more effectively. In this cell-crushing step, it is desired to use methods wherein no agents are used, such as ultrasonication method, homogenizer method, high-pressure crushing method, bead impact method, milling method, grinding method (wherein an assistant agent such as glass powders or alumina powders is added and ground in a mortar), and freeze-thawing method. In respect of this resuspension, a solid component and a soluble component are separated by a method such as centrifugal separation, and then a solid component containing a PHA component is treated with a peroxide compound or hypochlorite.

As stated above, in the present invention, hypochlorite can preferably be used as an oxidizing agent that solubilizes cell components other than PHA. A treatment with hypochlorite generates chlorine as a byproduct from the consumed hypochlorous ions, and a portion thereof adhered on the surface of water-insoluble PHA particles are separated. A portion weakly adhered on the surface of the PHA particles is eluted and removed by washing with water after a treatment with hypochlorite and solid-liquid separation, but a chlorine portion strongly adhered thereon becomes residual chlorine, and the residual chlorine is not removed until a heating process is performed. Such residual chlorine may be a problem for the use of the obtained PHA.

To remove such residual chlorine, in the present invention, after the above-stated treatment with hypochlorite and the subsequent solid-liquid separation step, there is further added a step of washing in a solution, wherein chlorine is soluble, set forth below. A washing treatment performed in a liquid has simple steps such as suspension or stirring, collection after washing is easy, and yield rate or purify is not reduced, so this washing treatment is suitable as a method for treating fine particles. It is needless to say that a washing solution is required not only to solubilize chlorine but also not to solubilize PHA. As a washing treatment for elimination of residual chlorine, there can be used means which comprises, further suspending the obtained PHA in a purified water, rising a temperature from 30° C. to 60° C. while stirring, removing chlorine remained in the collected PHA. In this case, the amount of a hot water is an amount in which the removed chlorine can sufficiently be dissolved, so 50 ml or more per g (dry weight) of PHA is desired, and a treating time is desirably 6 hours or more (it is desired that, as the treatment temperature is lowered, the treating time is lengthened). Moreover, it is desired that this treatment is repeated twice or more, while replacing the used hot water with new one.

After completion of the above-described washing, any method for collecting PHA particles in a washing solution can be applied, as long as the PHA particles can effectively be separated and purified from coexisting components by the method, and for example, centrifugal separation method can be applied.

As an alternative washing treatment for elimination of residual chlorine, there can be used the following means for washing residual chlorine with an aqueous thiosulfate solution to reduce the chlorine.

Thiosulfate used herein can be selected appropriately from a group consisting of potassium thiosulfate ($K_2S_2O_3$), potassium thiosulfate trihydrate ($K_2S_2O_3.3H_2O$), calcium thiosulfate hexahydrate ($CaS_2O_3.6H_2O$), ferrous thiosulfate ($FeS_2O_3$), sodium thiosulfate ($Na_2S_2O_3$), sodium thiosulfate pentahydrate ($Na_2S_2O_3.5H_2O$), and ammonium thiosulfate (($NH_4)_2S_2O_3$). Moreover, a solution or mixture comprising the above-listed thiosulfates can also be used.

Of these thiosulfates, sodium thiosulfate pentahydrate ($Na_2S_2O_3.5H_2O$, commonly called "hypo") has conventional been mainly used as a "kalk removing agent" from tap water. Sodium thiosulfate pentahydrate has an action to absorb chlorine in an aqueous solution, and the mechanism is shown in the following formula (1).

$$Na_2S_2O_3 + 4Cl_2 + 5H_2O \rightarrow 2NaCl + 2H_2SO_4 + 6HCl \qquad (1)$$

By washing PHA with an aqueous thiosulfate solution, residual chlorine retained by the PHA is removed as a result of the above reaction (1).

The temperature in a washing treatment with thiosulfate is set appropriately depending on the physical properties of the PHA, but it is usually set at 0° C. to 100° C., desirably 20° C. to 70° C. The washing time in the washing treatment is set at 5 minutes to 24 hours, desirably 1 hour to 3 hours.

After a washing treatment, any method for collecting PHA particles in a washing solution can be applied, as long as the PHA particles can effectively be separated and purified from coexisting components, and for example, centrifugal separation method can be applied. Further, it is more desirable if there is added a step of further washing the PHA particles washed by this washing treatment, with a purified water, or the like.

As an alternative washing treatment for elimination of residual chlorine, there can be used the following means for washing residual chlorine with an organic polar solvent to reduce the chlorine.

In this washing treatment with a polar solvent solution, residual chlorine adhered on the surface of PHA particles is washed with a polar solvent solution containing, at a concentration of 50% or more with respect to the total volume, an organic polar solvent that is insoluble to PHA of interest, so that the residual chlorine is eluted in the polar solvent solution and reduced.

Where the above-described washing treatment with an organic polar solvent is performed to a chlorine portion that is strongly adhered on the surface of insoluble PHA particles, most of the chlorine can be removed. In the PHA particles obtained by this method, the absolute amount of residual chlorine is significantly reduced. So, when a processed product is made using the PHA particles as raw materials, the amount of chlorine released by heating can be controlled to an extent where the chlorine does not become a factor of pollution of work environment, etc.

Examples of an organic polar solvent used in a washing treatment with a polar solvent solution include alcohol, ketone, etc. More specifically, such an organic polar solvent can be selected appropriately from methanol, ethanol, isopropanol, isobutanol, acetone, etc. for the use. Generally these organic polar solvents are used singly, but a mixed solvent comprising several types of solvents can also be used. Moreover, since the above-stated organic polar solvent such as alcohol or ketone has a high affinity with water, it can also be used as a mixed solvent obtained by being mixed with water uniformly. When an organic polar solvent is used as a mixed solvent that is mixed with water uniformly, it is desired that the content percentage (concentration) of the organic polar solvent is set high. For example, where the content percentage (concentration) of the organic polar solvent is set at 99% or more, a washing effect almost equivalent to the use of a single solvent can be achieved.

The temperature in a washing treatment with a polar solvent solution is set appropriately depending on the physical properties of PHA of interest such as solubility to an organic polar solvent, a softening point or melting point, but usually, it is desired to set at a temperature within a temperature domain where the organic polar solvent used is in a liquid state, allowing only a little transpiration, e.g. within a range of 0° C. to 50° C. The washing time in the washing treatment depends on the type of the used organic polar solvent or temperature, but it is set within a range of 5 minutes to 24 hours, preferably 1 hour to 3 hours to achieve sufficient washing and elimination.

After completion of a washing treatment with a polar solvent solution, as means for collecting the washed PHA particles from the liquid containing an organic polar solvent, any solid-liquid separation method can be applied, as long as the particles can effectively be separated from coexisting components dissolved in the polar solvent solution containing the organic polar solvent. For example, PHA particles can be separated from components dissolved in a solution containing an organic polar solvent by centrifugal separation method. Furthermore, after completion of the washing treatment with an organic polar solvent, it is more desirable if a step of further washing the collected PHA particles again with purified water or the like is added to remove the residue of the organic polar solvent.

It was found that, being independent of the type of PHA particles, a washing effect in the above-described washing treatment with a polar solvent solution has versatility and also high reproducibility. Moreover, since the amount of PHA particles is far smaller than the bulk of the original cells itself, the amount of an organic polar solvent used in the above-described washing treatment with the solvent is so little that it is incomparable with the amount of an organic solvent used in organic solvent extraction method. Furthermore, PHA itself is not dissolved but only chlorine adhered on a surface thereof is eluted, and the washed PHA particles are re-collected by solid-liquid separation method. So, in this step, the amount of an organic solvent that is volatilized or transpired can be kept extremely low. In organic solvent extraction method, a small amount of organic solvent remained even in a water phase should be collected, and further, when PHA was recovered from an organic phase, a large amount of organic solvent removed by solvent removal or the like should also be recovered. However, by the method of the present invention, a recovery of organic solvents that becomes more difficult as the scale increases, can be carried out easily.

In a step of drying the PHA particles obtained in the above-described step of removing residual chlorine, a method such as air drying, vacuum drying or freeze-drying can be selected as appropriate, depending on the physical properties of the PHA, the form to be taken, etc.

As an apparatus used to produce PHA by the above-described method, an apparatus used for general microorganism production or chemical synthesis can be used singly or in combination. An apparatus used to produce PHA having the following configurations can be exemplified as an embodiment of the production apparatus most suitable for the method for producing PHA of the present invention.

This apparatus has means for removing cell components other than PHA by treating cells comprising PHA with the above-described oxidizing agent; means for separating the treated cells into a water-soluble fraction and a water-insoluble fraction (PHA); and means for removing residual chlorine from the water-insoluble fraction by washing. The means for removing residual chlorine is at least one means selected from a group consisting of means for washing the water-insoluble fraction with a hot water, means for washing the water-insoluble fraction with an aqueous thiosulfate solution, and means for washing the water-insoluble fraction with a polar solvent solution comprising an organic polar solvent, which is insoluble to the above-described PHA. Moreover, this production apparatus can also be an apparatus having means for crushing cells comprising PHA to obtain a crushed product and means for separating the crushed product into a water-soluble fraction and a water-insoluble fraction, before the above-described means for treating with an oxidizing agent, as necessary.

The present invention will be further specifically described in the following examples. These are examples of the best mode for carrying out the present invention. However, these examples are not intended to limit the scope of the invention. The "%" in the following examples denotes weight standard, unless otherwise specified. An M9 medium used in each example has the following composition.

| (M9 medium) | |
|---|---|
| $Na_2HPO_4$ | 6.2 g |
| $KH_2PO_4$ | 3.0 g |
| NaCl | 0.5 g |
| $NH_4Cl$ | 1.0 g |

(pH 7.0 per liter of medium)

EXAMPLE 1

A colony of strain TB64 on an M9 agar medium containing 0.1% sodium malate was transferred to 50 ml of M9 medium containing 0.5% sodium malate in a 500 ml shaking flask, followed by shaking culture at 30° C. After 24 hours, 5 ml of the culture solution was added to 1 L of M9 medium wherein only $NH_4Cl$ as a nitrogen source was prepared at a concentration of 1/10, and which contained 0.5% sodium malate, and then the mixture was shaken in the same manner so as to accumulate PHB in cell bodies. After 52 hours, PHB accumulating cell bodies were collected by centrifugal separation and resuspended in 30 ml of distilled water, and then divided into three equal aliquots (10 ml each). These three aliquots were numbered 1 to 3 and the following treatment was carried out thereon.

1: Control: After centrifugal separation, one of the three aliquots was subjected to further washing with methanol, freeze-drying, and weighing. Then, an extraction with chloroform was carried out at 60° C. for 24 hours. After the obtained extract was filtrated and concentrated, it was reprecipitated with methanol followed by vacuum drying to obtain a control polymer (Sample 1).

2: Both 30 ml of deionized water cooled to 4° C. and 20 ml of sodium hypochlorite solution (containing 12% sodium hypochlorite (effective chlorine concentration: 5% or more); Kishida Chemical Co., Ltd.) cooled to 4° C., were added to one of the three aliquots, followed by reaction at 4° C. for 2 hours. After completion of the reaction, 140 ml of deionized water cooled to 4° C. was added to the reaction solution, and centrifugal separation was carried out at 4° C. at 29,400 m/s$^2$ (3,000×g) for 30 minutes. 80 ml of deionized water cooled to 4° C. was added to the obtained precipitate, and the particles were fully dispersed by ultrasonication followed by centrifugal separation (4° C., 29,400 m/s$^2$ (3,000×g), 30 minutes). This operation was repeated twice and the obtained precipitate was subjected to freeze-drying. The obtained product is defined as Sample 2.

3: A sample obtained by an operation of washing with deionized water as described in the above 2 was suspended in 50 ml of deionized water and stirred at 50° C. for 6 hours. Then, the supernatant was removed by centrifugal separation (4° C., 29,400 m/s$^2$ (3,000×g), 30 minutes). This washing treatment with a hot water was repeated once again. 40 ml of deionized water cooled to 4° C. was added to the obtained precipitate, and the particles were fully dispersed by ultrasonication, followed by centrifugal separation (4° C., 29,400 m/s$^2$ (3,000×g), 30 minutes). This operation was repeated once again and the obtained precipitate was subjected to freeze-drying. The obtained product is defined as Sample 3.

Measurement of Residual Chlorine

The residual chlorine of each of Samples 2 and 3 was measured as follows.

As shown in FIGURE, an Erlenmeyer flask 1 (the total content: 637ml), and a cap comprising an outer cap 2a (screw cap) having a hole in a center thereof, a Teflon inner cap 2b having a hole in a center thereof and aluminum foil 2c having the same size as the inner cap, were heated at 150° C. in an oven beforehand. Then, 0.3 g of a sample 4 on an aluminum foil 3 was placed into the flask and the cap was hermetically sealed, followed by heating at 150° C. After 3 minutes, a detector tube 6 (GASTEC Corp.; a chlorine detector tube, product No. 8La (detectable concentration: 0.5 ppm to 8 ppm) or product No. 8H (detectable concentration: 0.5 ppm to 8 ppm)) was inserted into the hole, and 100 ml gas generated from the sample was drawn from the tube to measure chlorine concentration.

As a result, the chlorine concentration of Sample 2 without a hot water treatment was about 50 ppm, whereas that of Sample 3 with a hot water treatment was about 4 ppm. When compared with Sample 2, Sample 3 has higher effects of chlorine reduction.

To determine "yield rate" and "purity" that are described below, the following operation was carried out.

30 ml of chloroform was added to Samples 1 to 3 that were dried, and a stirring extraction operation was carried out at 60° C. for 24 hours. The chloroform solution containing extracted PHB, was filtrated with a 0.45 μm PTFE filter, and the filtrate was concentrated by a rotary evaporator. The concentrate was added to 10 times amount of methanol to precipitate and collect PHB. The obtained PHB was subjected to vacuum drying and then weighing.

The weight ratio of the PHB obtained by extraction of Samples 2 and 3 with chloroform with respect to Sample 1 as a control, is determined as "yield rate", and the mass ratio of the PHB obtained by extraction of each sample with chloroform with respect to samples before chloroform extraction, is determined as "purity". The results are shown in Table 1.

TABLE 1

|  | Weight before chloroform extraction (mg/L) | Weight after chloroform extraction (mg/L) | Yield rate (%) | Purity (%) |
| --- | --- | --- | --- | --- |
| Sample 1 | 3100 | 1880 | — | — |
| Sample 2 | 1930 | 1820 | 96.8 | 94.8 |
| Sample 3 | 1920 | 1810 | 95.3 | 94.3 |

Although Sample 3 was treated with a hot water, the yield rate and purity of Sample 3 were almost the same as those of Sample 2 that was not treated with a hot water. Therefore, a treatment with a hot water has an effect of reducing residual chlorine, while keeping a high yield rate and a high purity.

EXAMPLE 2

A colony of *Pseudomonas oleovorans* on an M9 agar medium containing 0.1% n-nonanoic acid was transferred to 50 ml of M9 medium containing 0.3% n-nonanoic acid followed by shaking culture at 30° C. After 40 hours, 5 ml of the culture solution was added to 1 L of M9 medium containing 0.2% n-nonanoic acid and 0.05% 5-phenylvaleric acid, and then the mixture was subjected to shaking culture. After 36 hours, cell bodies were collected by centrifugal separation and resuspended in 1 L of M9 medium that did not contain $NH_4Cl$ as a nitrogen source but contained 0.05% n-nonanoic acid and 0.2% 5-phenylvaleric acid, and then a shaking was performed to accumulate in the cell bodies, PHA containing as units, 3-hydroxynonanoic acid, 3-hydroxyheptanoic acid, 3-hydroxyvaleric acid and 3-hydroxy-5-phenylvaleric acid. After 48 hours, cell bodies accumulating PHA were collected by centrifugal separation, and the following treatment was carried out thereon.

4: Control: After centrifugal separation, the cell bodies were subjected to washing with methanol, freeze-drying, and weighing. Then, a chloroform extraction was carried out at 60° C. for 24 hours. Thereafter, the extract was filtrated and concentrated, and then was reprecipitated with methanol followed by vacuum drying to obtain a control polymer (Sample 4).

5: Both 30 ml of deionized water cooled to 4° C. and 20 ml of sodium hypochlorite solution (containing 12% sodium hypochlorite (effective chlorine concentration: 5% or more); Kishida Chemical Co., Ltd.) cooled to 4° C., were added to the cell bodies, followed by a reaction at 4° C. for 2 hours. After completion of the reaction, 140 ml of deionized water cooled to 4° C. was added to the reaction solution, and centrifugal separation was carried out at 4° C. at 29,400 m/s² (3,000×g) for 30 minutes. 80 ml of deionized water cooled to 4° C. was added to the obtained precipitate, and the particles were fully dispersed by ultrasonication, followed by centrifugal separation (4° C., 29,400 m/s² (3,000×g), 30 minutes). This operation was repeated twice and the obtained precipitate was subjected to freeze-drying to obtain Sample 5.

6: A sample obtained by an operation of washing with a deionized water as described in the above 5, was suspended in 50 ml of deionized water and stirred at 30° C. for 12 hours. The supernatant was removed by centrifugal separation (4° C., 29,400 m/s² (3,000×g), 30 minutes), and then resuspended in 50 ml of deionized water, followed by stirring at 30° C. for 12 hours. After completion of the treatment, the supernatant was removed by centrifugal separation (4° C., 29,400 m/s² (3,000×g), 30 minutes), and 40 ml of deionized water cooled to 4° C. was added to the obtained precipitate. After the particles were fully dispersed by ultrasonication, centrifugal separation (4° C., 29,400 m/s² (3,000×g), 30 minutes) was carried out. This operation was repeated once again and the obtained precipitate was subjected to freeze-drying to obtain Sample 6.

The residual chlorine of each of Samples 5 and 6 was measured by the same method as described in Example 1. As a result, the chlorine concentration of Sample 5 without a hot water treatment was about 20 ppm (determined from 30 ml drawn by detector tube 8La), whereas that of Sample 6 with a hot water treatment was about 2 ppm. When compared with Sample 5, Sample 6 has higher effects of chlorine reduction.

Moreover, these samples were extracted with chloroform in the same manner as in Example 1, and the yield rate and the purity were determined. The results are shown in Table 2.

TABLE 2

|  | Weight before chloroform extraction (mg/L) | Weight after chloroform extraction (mg/L) | Yield rate (%) | Purity (%) |
| --- | --- | --- | --- | --- |
| Sample 4 | 1890 | 980 | — | — |
| Sample 5 | 1010 | 960 | 98.0 | 95.0 |
| Sample 6 | 1000 | 960 | 98.0 | 96.0 |

The yield rate and purity of Sample 6 with a hot water treatment are almost the same as those of Sample 5 that was not subjected to a hot water treatment. Therefore, similarly as in the case of PHB in Example 1, a hot water treatment has an effect of reducing residual chlorine with respect to PHA having an aromatic ring in this example, while keeping a high yield rate and a high purity.

EXAMPLE 3

Washing with Sodium Thiosulfate Aqueous Solution (1)

A strain YN2 was inoculated into 200 ml of M9 medium containing 0.5% yeast extract (Oriental Yeast, Co., Ltd.), and shaking culture was carried out at 30° C. at 125 strokes/min in a 500 ml of shaking flask. After 8 hours, the above culture solution was added to 25 L of M9 medium containing 0.5% polypeptone (Nihon Pharmaceutical Co., Ltd.) and 0.1% 5-thiophenoxyvaleric acid, and the mixture was then subjected to aeration and stirring culture at 30° C. for 48 hours in a 50 L jar fermenter.

200 ml of the above culture solution was subjected to centrifugal separation (78,000 m/s$^2$ (8,000×g), 4° C., 10 minutes) to collect microorganism cells, followed by washing with cold methanol and then vacuum drying. The pellet obtained by the vacuum drying was suspended in 20 ml of chloroform, and the suspension was stirred at 60° C. for 20 hours to extract PHA. The extract was filtrated with a membrane filter having a pore size of 0.45 μm and then concentrated with a rotary evaporator. The concentrate was reprecipitated in cold methanol, and then only the precipitate was collected and subjected to vacuum drying to obtain PHA. According to conventional methods, the obtained PHA was subjected to methanolysis, and analyzed by a Gas Chromatography/Mass Spectrometry (GC-MS, Shimadzu QP-5050, EI method) to identify a methyl esterified product of a PHA monomer unit. As a result, it was found that microorganism cells in the culture solution comprise PHA having a monomer unit composition shown in Table 3.

TABLE 3

| Polyhydroxyalkanoate produced by stain YN2 | |
|---|---|
| Dry weight of cell bodies (mg/L) | 1,300 |
| Weight of polymer (mg/L) | 530 |
| Monomer unit composition (GC-MS, TIC peak area ratio) | |
| 3-hydroxybutyric acid | 8.8% |
| 3-hydroxy-5-thiophenoxyvaleric acid | 91.2% |

Microorganism cells were collected from the culture solution other than that used in the above-described analyzing operation by centrifugal separation. The obtained cells were suspended in 1.6 L of purified water, and then 0.8 L of sodium hypochlorite solution (effective chlorine concentration: 5% or more) was added thereto. The mixed solution was shaken at 4° C. for 2 hours to solubilize cell components other than PHA, and then PHA was collected by centrifugal separation (29,400 m/s$^2$ (3,000×g), 4° C., 30 minutes). The obtained PHA was suspended in 200 ml of purified water. An operation of collecting PHA by centrifugal separation (29,400 m/s$^2$ (3,000×g), 4° C., 30 minutes) was repeated three times, and then washed with water to obtain PHA particles (Sample 7).

Residual chlorine retained by the PHA particles was evaluated by the following method.

(1) Organoleptic Evaluation

The chlorinous odor of the PHA particles left at room temperature was detected organoleptically, and evaluated it on a scale of 1 to 5:

+++(high), ++(medium), +(low), ±(feeble), −(none)

in the order of the strength of the chlorinous odor.

(2) Concentration Treatment

The above PHA particles were placed in a 500 ml capped flask, and the flask was completely sealed. After residual chlorine was released by heating for 1 hour in a 150° C. atmosphere, chlorine concentration in the flask was measured with a gas detector tube.

The results of evaluation of residual chlorine are shown in Table 4. The table shows that chlorine is remained in the PHA particles.

TABLE 4

| | | Organoleptic evaluation | Chlorine concentration (ppm) |
|---|---|---|---|
| Sample 7 | PHA particles | +++ | 20.0 |

1.0 g dry weight of PHA particles obtained by the above-described method was suspended in 50 ml of purified water and 50 ml of 10% aqueous sodium thiosulfate pentahydrate solution. After stirring these suspensions at 50° C. for 6 hours, PHA was collected from each suspension by centrifugal separation (29,400 m/s$^2$ (3,000×g), 4° C., 30 minutes). The obtained PHA was suspended in 40 ml of purified water and then an operation of collecting PHA by centrifugal separation (29,400 m/s$^2$ (3,000×g), 4° C., 30 minutes) was carried out three times. The obtained PHA was suspended in 10 ml of purified water and freeze-dried to obtain washed PHA particles. The PHA particles washed with purified water are defined as Sample 8, and those washed with 10% sodium thiosulfate pentahydrate solution are defined as Sample 9.

Residual chlorine retained by the washed PHA particles was evaluated by the following method.

(1) Organoleptic Evaluation

The chlorinous odor of the PHA particles left at room temperature was detected organoleptically, and evaluated it on a scale of 1 to 5:

+++(high), ++(medium), +(low), ±(feeble), −(none)

in the order of the strength of the chlorinous odor.

(2) Concentration Measurement

The above-described PHA particles were placed in a 500 ml capped flask, and the flask was completely sealed. After residual chlorine was released by heating for 1 hour in a 150° C. atmosphere, chlorine concentration in the flask was measured with a gas detector tube.

The results of evaluation of residual chlorine are shown in Table 5. From comparison made between Tables 4 and 5, it was found that a washing treatment with a hot purified water has an effect of reducing residual chlorine, but chlorine remained in the washed PHA particles is further reduced by washing with a sodium thiosulfate solution.

TABLE 5

| | | Organoleptic evaluation | Chlorine concentration (ppm) |
|---|---|---|---|
| Sample 8 | Purified water | ++ | 3.0 |
| Sample 9 | 10% aqueous sodium thiosulfate solution | − | <0.5 |

EXAMPLE 4

Washing with Aqueous Sodium Thiosulfate Solution (2)

1.0 g dry weight of PHA particles of Sample 7 obtained by the method in Example 3 was suspended in 50 ml each of 0%, 0.1%, 1.0% and 10% aqueous sodium thiosulfate pentahydrate solutions. These 4 types of suspensions were stirred at 50° C. for 6 hours, and then PHA was collected by centrifugal separation (29,400 m/s$^2$ (3,000×g), 4° C., 30 minutes). The obtained PHA was suspended in 50 ml of purified water and the suspension was further stirred at 50° C. for 6 hours, followed by centrifugal separation (29,400 m/s$^2$ (3,000×g), 4° C., 30 minutes) to collect PHA. The obtained PHA was suspended in 40 ml of purified water, and then an operation of collecting PHA by centrifugal separation (29,400 m/s$^2$ (3,000×g), 4° C., 30 minutes) was carried out three times. The obtained PHA was suspended in 10 ml of purified water and freeze-dried to obtain washed PHA particles. The PHA particles washed with 0%, 0.1%, 1.0% and 10% aqueous sodium thiosulfate solutions are defined as Samples 10, 11, 12 and 13, respectively.

Residual chlorine retained by the PHA particles was evaluated by the following method.
(1) Organoleptic Evaluation The chlorinous odor of the PHA particles left at room temperature was detected organoleptically, and evaluated it on a scale of 1 to 5:
+++(high), ++(medium), +(low), ±(feeble), −(none)
in the order of the strength of the chlorinous odor.
(2) Concentration Measurement The above washed particles were placed in a 500 ml capped flask, and the flask was completely sealed. After residual chlorine was released by heating for 1 hour in a 150° C. atmosphere, chlorine concentration in the flask was measured with a gas detector tube.

The results of evaluation of residual chlorine are shown in Table 6. From comparison made between Tables 4 and 6, it was found that a washing treatment with a hot purified water (a 0% aqueous sodium thiosulfate solution) has an effect of reducing residual chlorine, but residual chlorine in the washed PHA particles is further reduced by washing with a sodium thiosulfate solution though there is a subtle difference by organoleptic evaluation, and that the higher the concentration of sodium thiosulfate, the greater the effect can be obtained.

TABLE 6

|  |  | Organoleptic evaluation | Chlorine concentration (ppm) |
|---|---|---|---|
| Sample 10 | 0% aqueous sodium thiosulfate solution | + | <0.5 |
| Sample 11 | 0.1% aqueous sodium thiosulfate solution | ± | <0.5 |
| Sample 12 | 1.0% aqueous sodium thiosulfate solution | − | <0.5 |
| Sample 13 | 10% aqueous sodium thiosulfate solution | − | <0.5 |

EXAMPLE 5

Washing Treatment with Alcohol

A strain TL2 of *Alcaligenes* sp. Was inoculated into 1.6 L of M9 medium containing 0.5% sodium lactate, and shaking culture was carried out at 30° C. at 125 strokes/min. After 48 hours, cells were collected from the medium by centrifugal separation (78,000 m/s$^2$ (8,000×g), 4° C., 10 minutes).

The cells obtained by the above culturing operation were suspended in 80 ml of purified water, and 40 ml of sodium hypochlorite solution (effective chlorine concentration: 5% or more) was added thereto. This suspension was shaken at 4° C. for 2 hours to solubilize cell components other than PHA, and then PHA was collected by centrifugal separation (6,000×g, 4° C., 20 minutes). The collected PHA was resuspended in 40 ml of purified water, and an operation of collecting PHA particles by centrifugal separation (78,000 m/s$^2$ (8,000×g), 4° C., 10 minutes) was carried out twice. Then, PHA was washed with water to obtain PHA particles.

An aliquot of the obtained PHA was subjected to freeze-drying. Thereafter the aliquot was subjected to methanolysis according to conventional methods, and analyzed by a Gas Chromatography/Mass Spectrometry (GC-MS, Shimadzu QP-5050, EI method) to identify a methyl esterified product of a monomer unit constituting PHA. As a result of the identification, it was found that the obtained PHA is PHB having 3-hydroxybutyric acid as a monomer unit.

0.3 g dry weight of PHA particles obtained by the above process was suspended in 40 ml each of purified water, methanol, ethanol and isobutanol. These suspensions were stirred at 4° C. for 1 hour, and then PHA particles were collected by centrifugal separation (29,400 m/s$^2$ (3,000×g), 4° C., 20 minutes). The collected PHA particles were resuspended in 40 ml of purified water, and PHA particles were collected by centrifugal separation (78,000 m/s$^2$ (8,000×g), 4° C., 10 minutes). After the washing treatment, the obtained PHA particles were suspended in 10 ml of purified water, and then freeze-dried to obtain the PHA particles that underwent a washing treatment. The PHA particles washed with each of purified water, methanol, ethanol and isobutanol are defined as Samples 14, 15, 16 and 17, respectively.

In both a case where the above-described washed PHA particles (Samples 14 to 17) were left at room temperature and a case where the particles were heated, the amount of chlorine released from the particles was measured by the method stated below. The above-described washed particles were placed in a 50 ml vial, which was then completely sealed. After leaving at room temperature overnight, the amount of chlorine contained in a gas phase in the vial was measured with a gas detector tube. Then, after heating the vial on a hot plate at 150° C. for 2 minutes, the amount of chlorine contained in a gas phase in the vial was measured with a gas detector tube.

The results of measurement are shown in Table 7. From the results shown in the table, it was found that, when compared with the case of washing with a purified water (Sample 14), the amount of chlorine released from the PHA particles washed with alcohol (Samples 15 to 17) was reduced by about a half or more of both the case of being left at room temperature and the case of being heated.

TABLE 7

Effect of reducing residual chlorine in polyhydroxyalkanoate by alcohol washing

|  |  | Amount of chlorine released ($\mu$g) | |
|---|---|---|---|
|  |  | Left at room temperature | Heated at 150° C. for 2 minutes |
| Sample 14 | Purified water | >6.3 | 160 |
| Sample 15 | Methanol | 3.2 | 85 |
| Sample 16 | Ethanol | 1.3 | 54 |
| Sample 17 | Isobutanol | Nt | 25 |

Nt: Unmeasured

EXAMPLE 6

Washing Treatment with Ketone

A strain TL2 of *Alcaligenes* sp. was inoculated into 1.6 L of M9 medium containing 0.5% sodium lactate, and shaking culture was carried out at 30° C. at 125 strokes/min. After 48 hours, cells were collected from the medium by centrifugal separation (78,000 m/s² (8,000×g), 4° C., 10 minutes).

The cells obtained by the above culturing operation were suspended in 80 ml of purified water, and 40 ml of sodium hypochlorite solution (effective chlorine concentration: 5% or more) was added thereto. This suspension was shaken at 4° C. for 2 hours to solubilize cell components other than PHA, and then PHA was collected by centrifugal separation (6,000×g, 4° C., 20 minutes). The collected PHA was resuspended in 40 ml of purified water, and an operation of collecting PHA particles by centrifugal separation (78,000 m/s² (8,000×g), 4° C., 10 minutes) was carried out twice. Then, PHA was washed with water to obtain PHA particles.

An aliquot of the obtained PHA was subjected to freeze-drying. Thereafter the aliquot was subjected to methanolysis according to conventional methods, and then analyzed by a Gas Chromatography/Mass Spectrometry (GC-MS, Shimadzu QP-5050, EI method) to identify a methyl esterified product of a monomer unit constituting PHA. As a result of the identification, it was found that the obtained PHA is PHB having 3-hydroxybutyric acid as a monomer unit.

0.3 g dry weight of PHA particles obtained by the above process was suspended in 40 ml of purified water and 40 ml of acetone. These suspensions were stirred at 4° C. for 1 hour, and then PHA particles were collected by centrifugal separation (29,400 m/s² (3,000×g), 4° C., 20 minutes). The collected PHA particles were resuspended in 40 ml of purified water, and PHA particles were collected by centrifugal separation (78,000 m/s² (8,000×g), 4° C., 10 minutes). After the washing treatment, the obtained PHA particles were suspended in 10 ml of purified water, and then freeze-dried to obtain the PHA particles that underwent a washing treatment. The PHA particles washed with purified water, in both of the above washing treatments that carried out twice, are defined as Sample 18, and those washed with acetone in the first washing treatment are defined as Sample 19.

In both a case where the above-described washed PHA particles were left at room temperature and a case where the particles were heated, the amount of chlorine released from the particles was measured by the method stated below. The above-described washed particles were placed in a 50 ml vial, which was then completely sealed. After leaving at room temperature overnight, the amount of chlorine contained in a gas phase in the vial was measured with a gas detector tube. Then, after heating the vial on a hot plate at 150° C. for 2 minutes, the amount of chlorine contained in a gas phase in the vial was measured with a gas detector tube.

The results of measurement are shown in Table 8. From the results shown in the table 8, it was found that, when compared with the case of washing with a purified water (Sample 18), the amount of chlorine released from the PHA particles washed with acetone (Sample 19) was significantly reduced, that is, the amount of chlorine still remained in the PHA particles after a washing treatment was sharply reduced.

TABLE 8

Effect of reducing residual chlorine in polyhydroxyalkanoate by acetone washing

| | | Amount of chlorine released (μg) | |
|---|---|---|---|
| | | Left at room temperature | Heated at 150° C. for 2 minutes |
| Sample 18 | Purified water | >6.3 | 160 |
| Sample 19 | Acetone | 1.6 | 32 |

EXAMPLE 7

Crushing Treatment (1)

A colony of strain TB64 on an M9 agar medium containing 0.1% sodium malate was transferred to 50 ml of M9 medium containing 0.5% sodium malate in a 500 ml shaking flask, followed by shaking culture at 30° C. After 24 hours, 5 ml of the culture solution was added to 1 L of M9 medium wherein only $NH_4Cl$ as a nitrogen source was prepared at a concentration of 1/10, and which contained 0.5% sodium malate, and then the mixture was shaken in the same manner to accumulate PHB in cell bodies. After 48 hours, PHB accumulating cell bodies were collected by centrifugal separation and resuspended in 50 ml of distilled water, and then divided into five equal aliquots (10 ml each). Each of the five aliquots was subjected to each of the following 5 types of treatments (20 to 24).

20: Control: One of the five equal aliquots was subjected to centrifugal separation and then washed with methanol, followed by freeze-drying and weighing. Then, an extraction with chloroform was carried out at 60° C. for 24 hours. After the obtained extract was filtrated and concentrated, it was reprecipitated with methanol followed by vacuum drying to obtain a control polymer (Sample 20).

21: 40 ml of 31% hydrogen peroxide solution (Mitsubishi Gas Chemical Company, Inc.; JIS K-8230) was added to another of the five equal aliquots followed by a treatment at 80° C. for 1 hour.

22: Distilled water was added to another of the above five equal aliquots to make the total amount 50 ml, and French press (Ohtake Works; French Press 5501) was carried out thereon, followed by centrifugal separation at 4° C. at 29,400 m/s² (3,000×g) for 30 minutes. Thereafter, 40 ml of distilled water was further added thereto, and then centrifugal separation was carried out at 4° C. at 29,400 m/s² (3,000×g) for 30 minutes, followed by washing.

23: Another of the above five equal aliquots was subjected to the same operation as described in the above 22, and then the obtained precipitated portion was suspended in 10 ml of distilled water and 40 ml of 31% hydrogen peroxide solution was added thereto, followed by a treatment at 80° C. for 1 hour.

24: Final one of the above five equal aliquots was subjected to the same operation as described in the above 22, and then the obtained precipitated portion was suspended in 10 ml of distilled water, and 5 ml of sodium hypochlorite solution (Kishida Chemical Co., Ltd.; containing 12% sodium hypochlorite (effective chlorine concentration: 5% or more)) was added thereto, followed by a treatment at 4° C. for 2 hours.

The above five aliquots, each of which was subjected to treatments described in the above 21 to 24 separately, were subjected to centrifugal separation (4° C., 29,400 m/s² (3,000×g), 30 minutes), and cooled to 4° C. again. After 40 ml of distilled water was added thereto and fully stirred, centrifugal separation was carried out twice under the same conditions and the obtained precipitate was subjected to freeze-drying and then weighing. The obtained products are defined as Samples 21 to 24, respectively.

To evaluate "yield rate" and "purity" that are stated below, the following operation was carried out.

30 ml of chloroform was added to Samples 20 to 24 that were freeze-dried, and a stirring extraction operation was carried out at 60° C. for 24 hours. The chloroform solution containing extracted PHB, was filtrated with a 0.45 μm PTFE filter, and the filtrate was concentrated with a rotary evaporator. The concentrate was added to 10 times amount of methanol to precipitate and collect PHB. The obtained PHB was subjected to vacuum drying and then weighing.

The weight ratio of the PHB obtained by extracting Samples 21 to 24 with chloroform with respect to Sample 20 as a control, is determined as "yield rate", and the weight ratio of the PHB obtained by extracting each sample with chloroform with respect to samples before chloroform extraction, is determined as "purity". The results are shown in Table 9.

TABLE 9

| | Weight before chloroform extraction (mg/L) | Weight after chloroform extraction (mg/L) | Yield rate (%) | Purity (%) |
|---|---|---|---|---|
| Sample 20 | 2900 | 1830 | — | — |
| Sample 21 | 1940 | 1790 | 97.8 | 92.3 |
| Sample 22 | 2020 | 1810 | 98.9 | 89.6 |
| Sample 23 | 1800 | 1760 | 96.2 | 97.8 |
| Sample 24 | 1830 | 1770 | 96.7 | 96.7 |

There is not a significant difference in respect of yield rate. In respect of purity, however, when compared with Sample 21 treated with no French press but treated with a hydrogen peroxide solution and Sample 22 treated with French press but treated with no hydrogen peroxide solution, Sample 23 treated with both French press and a hydrogen peroxide solution and Sample 24 treated with French press and hypochlorite had good results. It is clear that purity is improved by the combined use of a crushing treatment and an oxidizing agent treatment.

The molecular weight of the obtained PHB was measured by gel permeation chromatography (GPC; Tosoh HLC-8020, column: Polymer Laboratory PLgelMIXED-C (5 μm), solvent: chloroform, converted to polystyrene). The results are shown in Table 10.

TABLE 10

| | Mn | Mw | Mw/Mn |
|---|---|---|---|
| Sample 20 | 550000 | 1250000 | 2.3 |
| Sample 21 | 510000 | 1230000 | 2.4 |
| Sample 22 | 540000 | 1200000 | 2.2 |
| Sample 23 | 500000 | 1210000 | 2.4 |
| Sample 24 | 490000 | 1230000 | 2.5 |

There were observed almost no differences among the molecular weights of each sample. It is clear that there is a smaller change of molecular weight by a disruption treatment or an oxidizing agent treatment, when compared with the conventional chloroform extraction methods.

EXAMPLE 8

Crushing Treatment (2)

A colony of Pseudomonas oleovorans on an M9 agar medium containing 0.1% n-nonanoic acid was transferred to 50 ml of M9 medium containing 0.3% n-nonanoic acid followed by shaking culture at 30° C. After 40 hours, 5 ml of the culture solution was added to 1 L of M9 medium containing 0.1% n-nonanoic acid and 0.1% 5-phenylvaleric acid, followed by shaking culture. After 40 hours, cell bodies were collected by centrifugal separation and resuspended in 1 L of M9 medium that did not contain $NH_4Cl$ as a nitrogen source, but contained 0.1% n-nonanoic acid and 0.1% 5-phenylvaleric acid. The suspension was shaken in the same manner, so as to allow the cell bodies to accumulate PHA comprising, as units, 3-hydroxynonanoic acid, 3-hydroxyheptanoic acid, 3-hydroxyvaleric acid and 3-hydroxy-5-phenoxyvaleric acid. After 40 hours, the cell bodies accumulating PHA were collected by centrifugal separation, and resuspended in 40 ml of distilled water in the same manner as in Example 7. The suspension was then divided into four equal aliquots (10 ml each), and these aliquots were subjected to the following 4 types of treatments (25 to 28), separately.

The treatments are as follows.

25: Control: One of the above four equal aliquots was subjected to centrifugal separation and then washed with methanol, followed by freeze-drying and weighing. Then, chloroform extraction was carried out at 60° C. for 24 hours. After the obtained extract was filtrated and concentrated, it was reprecipitated with methanol followed by vacuum drying to obtain a control polymer (Sample 25).

26: 40 ml of 31% hydrogen peroxide solution (Mitsubishi Gas Chemical Company, Inc.; JIS K-8230) was added to another of the above four equal aliquots, followed by a treatment at 80° C. for 1 hour.

27: Some amount of distilled water was added to another of the above four equal aliquots to have the total amount of 50 ml, and French press (Ohtake Works; French Press 5501) was carried out thereon, followed by centrifugal separation at 4° C. at 29,400 m/s² (3,000×g) for 30 minutes. Thereafter, 40 ml of distilled water was further added thereto, and then centrifugal separation was carried out at 4° C. at 29,400 m/s² (3,000×g) for 30 minutes, followed by washing.

28: Final one of the above four equal aliquots was subjected to the same operation as described in the above 27, and then the obtained precipitated portion was suspended in 10 ml of distilled water and 40 ml of 31% hydrogen peroxide solution was added thereto, followed by a treatment at 80° C. for 1 hour.

The aliquots, 26 to 28, were subjected to centrifugal separation (4° C., 29,400 m/s² (3,000×g), 30 minutes), and then 40 ml of distilled water was added thereto and fully stirred. Thereafter, centrifugal separation was carried out twice under the same conditions and the obtained precipitate was subjected to freeze-drying and then weighing. The obtained products are defined as Samples 26 to 28.

These samples were subjected to chloroform extraction in the same manner as in Example 7, and "yield rate" and "purity" were determined. The results are shown in Table 11.

TABLE 11

|  | Weight before chloroform extraction (mg/L) | Weight after chloroform extraction (mg/L) | Yield rate (%) | Purity (%) |
| --- | --- | --- | --- | --- |
| Sample 25 | 1980 | 1080 | — | — |
| Sample 26 | 1210 | 1000 | 92.6 | 83.4 |
| Sample 27 | 1230 | 1010 | 93.5 | 82.1 |
| Sample 28 | 1110 | 990 | 91.7 | 89.2 |

There is not a significant difference in respect of yield rate. In respect of purity, however, when compared with Sample 26 treated with no French press but treated with a hydrogen peroxide solution and Sample 27 treated with French press but treated with no hydrogen peroxide solution, the purity of Sample 28 treated with both French press and a hydrogen peroxide solution was the highest. It is clear that, similarly as in the case of PHB shown in Example 7, the purity of PHA having an aromatic ring as shown in this example is also improved by the combined use of a crushing treatment and an oxidizing agent treatment.

The molecular weight of the obtained PHB was measured by gel permeation chromatography (GPC; Tosoh HLC-8020, column: Polymer Laboratory PLgelMIXED-C (5 μm), solvent: chloroform, converted to polystyrene). The results are shown in Table 12.

TABLE 12

|  | Mn | Mw | Mw/Mn |
| --- | --- | --- | --- |
| Sample 25 | 35000 | 91000 | 2.6 |
| Sample 26 | 32000 | 89000 | 2.8 |
| Sample 27 | 34000 | 90000 | 2.6 |
| Sample 28 | 30000 | 89000 | 3.0 |

There were observed almost no differences among the molecular weight of each sample. It is clear that, in respect of PHA having an aromatic ring also, there is no change in molecular weight by a crushing treatment or an oxidizing agent treatment, when compared with the conventional chloroform extraction methods.

According to the method of the present invention, it becomes possible to simply obtain polyhydroxyalkanoate accumulated in cells of microorganisms or the like with high yield, while maintaining the original molecular weight. Moreover, using the method for producing PHA of the present invention, PHA particles having reduced residual chlorine can efficiently be produced on an industrial scale, without using means for organic solvent extraction.

The particles of polyhydroxyalkanoate obtained by the method of the present invention will be raw materials useful as biodegradable materials, biocompatible materials, various functional materials, etc., and can be expected to be applied to various fields such as device materials or medical materials.

What is claimed is:

1. A method for producing polyhydroxyalkanoate, comprising:
   a step of treating cells containing polyhydroxyalkanoate with an oxidizing agent containing at least hypochlorite;
   a step of separating the treated cells into a water-soluble fraction and a water-insoluble fraction; and
   a step of reducing chlorine remaining in the water-soluble fraction by washing said water-insoluble fraction with an aqueous thiosulfate solution.

2. The method for producing polyhydroxyalkanoate according to claim 1, wherein a concentration of said hypochlorite is within a range of 1.5% to 5.0% as an effective chlorine concentration.

3. The method for producing polyhydroxyalkanoate according to claim 1, wherein said hypochlorite is sodium hypochlorite.

4. The method for producing polyhydroxyalkanoate according to claim 1, wherein said step of reducing chlorine is a step of washing said water-insoluble fraction with a liquid in which chlorine is soluble.

5. The method for producing polyhydroxyalkanoate according to claim 1, wherein said step of reducing chlorine is a step of washing said water-insoluble fraction with a hot water.

6. The method for producing polyhydroxyalkanoate according to claim 5, wherein a temperature of said hot water is within a range of 30° C. to 60° C.

7. The method for producing polydroxyalkanoate according to claim 1, further comprising a step of washing the obtained polyhydroxyalkanoate with a hot water.

8. The method for producing polyhydroxyalkanoate according to claim 1, wherein said thiosulfate is at least one selected from the group consisting of potassium thiosulfate, potassium thiosulfate trihydrate, calcium thiosulfate hexahydrate, ferrous thiosulfate, sodium thiosulfate, sodium thiosulfate pentahydrate and ammonium thiosulfate.

9. The method for producing polyhydroxyalkanoate according to claim 1, wherein said step of reducing chlorine is a step of washing said water-insoluble fraction with a polar solvent solution containing at least an organic polar solvent in which said polyhydroxyalkanoate is insoluble.

10. The method for producing polyhydroxyalkanoate according to claim 9, wherein said organic polar solvent is at least one selected from the group consisting of alcohols and ketones.

11. The method for producing polyhydroxyalkanoate according to claim 10, wherein said alcohol is at least one selected from the group consisting of methanol, ethanol, isopropanol and isobutanol.

12. The method for producing polyhydroxyalkanoate according to claim 10, wherein said ketone is acetone.

13. The method for producing polyhydroxyalkanoate according to claim 1, further comprising:
   a step of obtaining a crushed product by crushing cells containing polyhydroxyalkanoate; and
   a step of separating the crushed product into a water-soluble fraction and a water-insoluble fraction,
   where said water-insoluble fraction is used in said step of treating with an oxidizing agent.

14. The method for producing polyhydroxyalkanoate according to claim 13, wherein said step of obtaining the crushed product by crushing cells is performed by at least one selected from the group consisting of ultrasonication method, homogenizer method, high-pressure crushing method, bead impact method, milling method, grinding method, and freeze-thawing method.

15. The method for producing polyhydroxyalkanoate according to claim 1, wherein said polyhydroxyalkanoate is poly-3-hydroxybutyric acid.

* * * * *